United States Patent
Tanaka et al.

(10) Patent No.: US 6,703,053 B2
(45) Date of Patent: Mar. 9, 2004

(54) ANTI-HSV AGENT FOR INHIBITING REPLICATION OF HSV-1 AND HSV-2 AND METHOD OF PRODUCING A SUBSTANCE HAVING ANTI-HSV ACTIVITY

(75) Inventors: Akiko Tanaka, St. Petersburg, FL (US); John Jessip, St. Petersburg, FL (US); Amy Sears, St. Petersburg, FL (US)

(73) Assignee: Tampa Bay Research Institute, St. Petersburg, FL (US)

( * ) Notice: Subject to any disclaimer, the term of this patent is extended or adjusted under 35 U.S.C. 154(b) by 56 days.

(21) Appl. No.: 10/000,476

(22) Filed: Oct. 24, 2001

(65) Prior Publication Data

US 2003/0086992 A1 May 8, 2003

(51) Int. Cl.⁷ ................................................. A61K 35/78
(52) U.S. Cl. ........................................ 424/770; 424/776
(58) Field of Search .................................. 424/770, 776

(56) References Cited

U.S. PATENT DOCUMENTS 5,698,524 A * 12/1997 Mach et al.
5,929,047 A * 7/1999 Nakano

OTHER PUBLICATIONS

Lai et al. J. Gen. Appl. Microbiol. 1992. vol. 38, pp. 303–312.*
Fukuchi et al. Anticancer Res. 1989. vol. 9, pp. 313–318.*
Sakagami et al. Anticancer Res. 1991. vol. 11, pp. 881–888.*

* cited by examiner

*Primary Examiner*—Christopher R. Tate
(74) *Attorney, Agent, or Firm*—Pendorf & Cutliff

(57) ABSTRACT

An anti-HSV agent that inhibits the replication of HSV-1 and HSV-2 that is derived from a plant. Further, provided is a method of producing a potassium hydroxide extract of pine cone having anti-HSV activity, and the Anti-HSV agent.

10 Claims, 3 Drawing Sheets ug/ml PCE

ANTI-HSV AGENT FOR INHIBITING REPLICATION OF HSV-1 AND HSV-2 AND METHOD OF PRODUCING A SUBSTANCE HAVING ANTI-HSV ACTIVITY

FIELD OF INVENTION

The present invention relates to an anti-HSV agent derived from a plant that inhibits the replication of HSV-1 AND HSV-2 and a method for producing a plant-derived substance that has Anti-HSV activity.

BACKGROUND OF THE INVENTION

Infections by Herpes simplex virus (HSV), Herpes simplex virus Type I, and Herpes simplex virus Type II, affect approximately 50 million Americans and about 500,000 new cases appear each year. Approximately 30 million Americans are infected with genital herpes (American Social Health Association). The HSV virion is a large (100 to 150 m.gamma.), enveloped virus with an icosahedral capsid. It has double stranded DNA with a genome that encodes at least 70 polypeptides. This large amount of regulatory information permits the virus to control its own gene expression and to modify multiple complex events within the infected cell. The herpes simplex virus enters the host by direct contact, is spread to a target tissue only, spreads within the host via neuronal axonal flow, targets the dorsal root ganglia and after recovery of the host from an acute infection, remains latent in the targeted tissue. HSV viruses are difficult to treat because they appear to have a mechanism by which they are able, over several generations of the virus, to adapt to adverse environmental conditions and survive.

Once the virus is transmitted to a susceptible individual, HSV replicates in the epithelial cells of mucosal surfaces. The HSV replication is usually asymptomatic, as evidenced by the many individuals who are seropositive for HSV antibody, but have no history of symptomatic infection. For some individuals the infection can result in severe, ulcerative lesions.

Following replication in epithelia, the virus infects the peripheral endings of the sensory neurons innervating the site of infection, and is transported through the neuronal axons to the nuclei. Viral DNA enters the neuronal nuclei and latent infections are established. Because the latent infection remain in those nerve cells of the body for the lifetime of the host, infection by HSV has the potential to result in many episodes of recurrent disease and transmission.

The use of pharmaceutical and herbal treatments of the HSV-1 and HSV-2 viruses is known in the prior art. More specifically, treatments are focused on HSV-1, the primary cause of cold sores, or HSV-2, the main cause of genital herpes. Epidemiologic studies have suggested that infection by HSV-2, along with other sexually transmitted diseases that cause genital ulcers, increases the risk of acquisition of HIV. The mechanism of this increased risk is unknown, but it may be due to the increased numbers of HIV-susceptible cells (CD4+ T cells and macrophages) present in genital epithelium during inflammatory immune responses generated by the STDs (Latif et al. 1989).

The treatments currently available help the host immune system to help itself in coping with the herpes virus. Most of the present treatments are focused upon preventing the fusion of the virion envelope with the host cell plasma membrane by negatively influencing host cell membrane receptors or by interfering with the glycosylation of viral protein required for fusion, and by reducing viral replication within the host cell nucleus. There are a number of antiviral drugs available for inhibition of HSV replication, including acyclovir, gancyclovir and foscarnet. Three of the most popular medications prescribed to treat genital herpes are: Acyclovir, Famciclovir and Valacyclovir.

Acyclovir (ACV), 9-[(2-hydroxyethoxy)methyl]guanine, is a major antiviral drug which has been used in the treatment of a variety of herpes virus infections. It can be administered as topical, oral, or intravenous preparations, the topical preparations being less effective. Acyclovir therapy is associated with very few adverse effects. Valaciclovir or L-valine ester of acyclovir is a prodrug of acyclovir. The antiherpes virus agent penciclovir, 9-(4-hydroxy-3-hydroxymethylbut-1-yl)-guanine, has a spectrum of activity against human herpes viruses similar to that of acyclovir. Famciclovir, the 6-deoxy derivative of penciclovir, is converted to penciclovir in the body by means of oxidative metabolism.

Nucleoside analogues such as the guanosine analogues acyclovir, valaciclovir, penciclovir and famciclovir have a more narrow antiviral spectrum than foscarnet and mainly show effect against HSV-1 and HSV-2 and VZV viruses. These compounds do not act directly on the viral DNA polymerase like foscarnet, but have to be phosphorylated three times by viral and cellular enzymes for inhibition of the viral polymerase to be achieved. They are primarily administered as oral compositions although other ways of administration, such as parenteral, are also possible. Some problems in treating herpes virus infections by parenteral administration are the high doses and large volumes to be administered and the short half-life of the antiviral compound in the circulation. Further, they require daily administration of the drugs for long periods of time. The clinical effectiveness of the nucleoside analogues acyclovir, valaciclovir, penciclovir and famciclovir on recurrent cutaneous virus diseases is, as with foscarnet, limited. With topical treatment, the healing time is only reduced by approximately two to three days.

It should be noted that all of the above drugs target replication of the viral DNA following infection of susceptible cells. They have been shown ineffective at reducing viral replication in genital epithelium when applied topically after infection has proceeded to the extent of causing lesions. Reduction of epithelial replication during initial infection has been demonstrated in animal models to reduce the amount of latent virus present in ganglia and to reduce the frequency and severity of recurrent disease. However, other studies have demonstrated that epithelial replication is not a prerequisite for the establishment of latent infection in animal models. Further, the high percentage of women with latent virus but no history of symptomatic infection suggests that in humans, high levels of replication may not be necessary for the establishment of latency.

In addition to the drugs that are set out above, many herbal treatments are being used and their effectiveness continuously being studied. The active ingredient in most herbs is an alkaloid, a very toxic molecule if taken in considerable excess. There are several herbs that are more than a match for most viruses, examples being; lavender, myrrh and sage.

There are even instances where natural essential oils have strong powerful results against the HSV virus on contact. The active ingredients vary from Terpenes, Sesquiterpenes through to Ketones, Aldehydes, Esters, to Alcohols, and phenols. Generally, the essential oils are the refined active ingredients from flowers, leaves and roots of plants. The most commonly used are lavender, basil, calendula, lemon, tee tree, cinnamon, citronella, clove, eucalyptus, geranium, niqouli, oregano, peppermint, thyme, ginger, patchouli, cedar wood, Melissa, cajeput, rosemary and many others.

The results of this resurgence in the use of herbal and natural products, has prompted numerous studies to investigate the biological basis for medicinal properties associated herbals. One such plant product that has potential medicinal properties is an extract of pinecones. The pine cone extract has been reported to have an ameliorative effect on a variety of infectious diseases and on several tumors.

The alkaline extraction of a pinecone is taught by U.S. Pat. No. 4,985,249. In that patent alkaline extraction is followed by pH 5 precipitation to yield a fraction known and PC6; further precipitation by alcohol resulted in another fraction termed PC7. The active components of both fractions, PC6 and PC7, have been shown to contain lignins or polyphenylpropenoids covalently linked with polysaccharides. Further, U.S. Pat. No. 4,985,249 has been proven to have inhibitory activity in vitro against human immunodeficiency virus (HIV) replication.

In order to provide an effective treatment to reduce the levels of replication of HSV-1 and HSV-2 following the primary and reactivated infections, the present inventors have assessed the anti-HSV activity of potassium hydroxide extract of pine cone.

The addition of potassium with the pine cone extract improves the general health benefits of the anti-HSV agent. It is known that potassium is an extremely important electrolyte in the body that functions in the maintenance of: water balance and distribution; acid-base balance; muscle and nerve cell function; heart function, and kidney and adrenal function.

Therefore, it can be appreciated that there exists a continuing need for a new and improved anti HSV agent which can be used to solve the problem of viral replication and reactivation which remains unsolved by the prior art. In this regard, the present invention fulfills this need.

BRIEF SUMMARY OF THE INVENTION

The present invention is a method of inhibiting replication of HSV-1 AND HSV-2 using an anti-HSV agent derived from a plant viz a potassium hydroxide extraction method for producing an extract of pine cone that has anti-HSV activity and contains potassium.

After extensive study and testing the inventor discovered that, a high yield of extract from pinecone is obtained by using a potassium hydroxide solution. Further, the inventor discovered that the resulting extract, termed the polyphenylpropenoid-polysaccharide complex (PPC or PCE) has antiviral activity. Accordingly, a primary function of the present invention is to provide a plant-derived substance, which has potent anti-HSV activity.

Another object of the present invention is to provide a method of inhibiting replication of HSV-1 AND HSV-2 using the plant-derived anti-HSV agent.

Still another object of the present invention is to provide a method for obtaining the anti-HSV substance from pine cones.

An even further object of the present invention is to provide an anti-HSV agent which includes potassium.

It is the object of the invention to provide a method for the production of a pine cone extract. It is a further object of the invention to provided a pine cone extract produced by that method.

The anti-HSV agent of the present invention is characterized in that said agent contains a potassium hydroxide extract of various pine cones such as *Pinus parviflroa* Sieb. Et Zucc., especially high molecular weight anti-HSV substances of this extract. The high molecular weight anti-HSV substances describe above can be obtained by extraction of the pine cone with a potassium hydroxide solution.

A further object of the present invention is to provide a new and improved method of inhibiting replication of HSV-1 AND HSV-2 using an ANTI-HSV agent which may be easily and efficiently manufactured and marketed.

An even further object of the present invention is to provide a method for producing a potassium hydroxide extract of pine cone that has anti-HSV activity which is susceptible of a low cost of manufacture with regard to both materials and labor, and which accordingly is then susceptible of low prices of sale to the consuming public, thereby making such method of producing a pine cone extract with anti-HSV activity economically available to the buying public.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated the preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Figure 1:
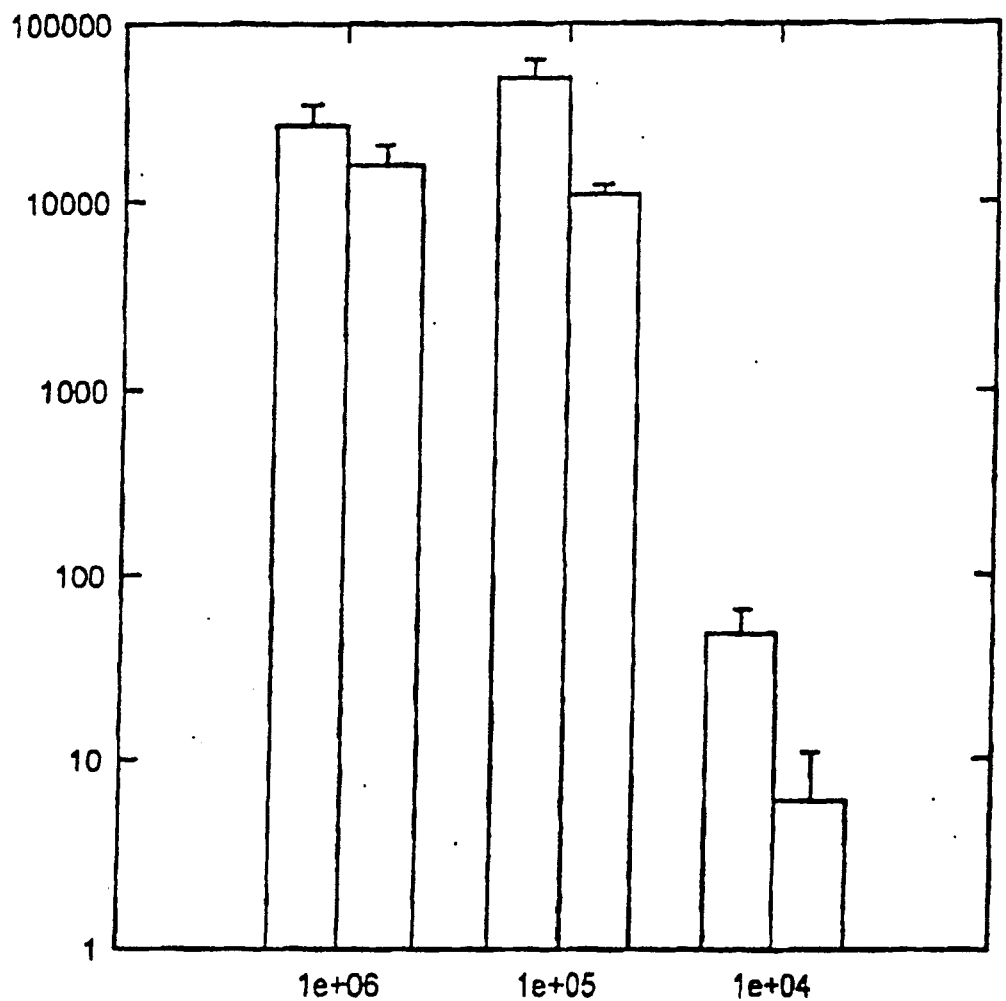
FIG. 1 shows the average titers of eyes 24 hours after infection with varying amounts of virus.

Plants have been a major source of medicinal compounds for thousands of years. Chemical components and analogs which have been derived from plant materials now comprise a major portion of the medicines in clinical use. One such plant product is derived from the pine cones of various pine trees. Any commercially available pine cone material can be used for the preparation of anti-HSV substances. The substances with a certain extent of activity can be extracted from pine cone with an aqueous alkaline solution of KOH. The substances which are contained in the extract and used as active ingredients are high molecular weight substances. The most potent substances were named PPC or PCE.

The extracted solution should be concentrated to the desired concentration, if needed neutralized with appropriate acid and then lyophilized to give appropriate concentrated solution or solid. These can be used as active components without further fractionation. The substance that is not further processed is to be refrigerated.

As far as the present invention is concerned, useful pine cones can be of any species and variety of genus Pinus, especially those of table 1, without intended limitation to the correctness of the taxonomical classification of that table. Preferred pine cones are those of *P. densiflora, P. koraiensis, P. parviflora* and *P. thunbergii*. The inventors have found that pine cones in general and pine cones of the preferred species in particular contain substances and compositions (active ingredients) useful in vaccination and/or therapy methods.

TABLE 1

Pines producing pine cones useful for preparing pine cone extracts

| | |
|---|---|
| Subgenus Pinus | |
| Section Pinus, Subsection Pinus | *P. densata, P. densiflora, P. heldreichii, P. hwangshanensis, P. kesiya, P. luchuensis, P. massoniana, P. mugo, P. nigra, P. resinosa, P. sylvestris, P. tabuliformis, P. thunbergii, P. tropicalis, P. yunnanensis* |
| Section Pinea, Subsection Pinaster Loudon | *P. brutia, P. canariensis, P. halepensis, P. latteri, P. merkusii, P. pinaster, P. roxburghii* |
| Section Pinea, Subsection Pineae Little & Critchfield | *P. pinea* |
| Section Trifoliis, Subsection Contortae Little & Critchfield | *P. banksiana, P. contorta* |
| Section Trifoliis, Subsection Australes Loudon | *P. caribaea, P. clausa, P. cubensis, P. echinata, P. elliottii, P. glabra, P. occidentalis, P. palustris, P. pungens, P. rigida, P. serotina, P. taeda, P. virginiana* |
| Section Trifoliis, Subsection Ponderosae Loudon | 'Sabinianae Group': *P. coulteri, P. sabiniana, P. torreyana* 'Ponderosa Group': *P. arizonica, P. durangensis, P. engelmannii, P. jeffreyi, P. ponderosa, P. washoensis* 'Montezumae Group': *P. devoniana, P. hartwegii, P. montezumae* 'Pseudostrobus Group': *P. douglasiana, P. maximinoi, P. pseudostrobus* |
| Section Trifoliis, Subsection Oocarpae Little & Critchfield | 'Attenuata Group': *P. attenuata, P. muricata, P. radiata* 'Oocarpa Group': *P. greggii, P. jaliscana, P. oocarpa, P. patula, P. praetermissa, P. pringlei, P. tecunumanii* 'Teocote Group': *P. herrerae, P. lawsonii, P. teocote* |
| Section Trifoliis, Subsection Leiophyllae Loudon | *P. leiophylla, P. lumholtzii* |
| Subgenus Ducampopinus | |
| Section Ducampopinus, Subsection Krempfianae Little & Critchfield | *P. krempfii* |
| Section Gerardiana, Subsection Gerardianae Loudon | *P. bungeana, P. gerardiana, P. squamata* |
| Section Parryana, Subsection Nelsoniae Van der Burgh | *P. nelsonii* |
| Section Parryana, Subsection Rzedowskianae Carvajal | *P. maximartinezii, P. pinceana, P. rzedowskii* |
| Section Parryana, Subsection Cembroides Engelmann | *P. cembroides, P. culminicola, P. discolor, P. edulis, P. johannis, P. juarezensis, P. monophylla, P. orizabensis, P. remota* |

TABLE 1-continued

Pines producing pine cones useful for preparing pine cone extracts

| | |
|---|---|
| Section Parryana, Subsection Balfourianae Engelmann Subgenus Strobus | *P. aristata, P. balfouriana, P. longaeva* |
| Section Strobus, Subsection Strobi Loudon | *P. amamiana, P. armandii, P. ayacahuite, P. bhutanica, P. chiapensis, P. dalatensis, P. fenzeliana, P. flexilis, P. lambertiana, P. monticola, P. morrisonicola, P. parviflora, P. peuce, P. pumila, P. strobiformis, P. strobus, P. wallichiana, P. wangii* |
| Section Strobus, Subsection Cembrae Loudon | *P. albicaulis, P. cembra, P. koraiensis, P. sibirica* |

The present invention will be explained by the following examples, however, the invention will not be restricted to these examples.

Purification Procedure of PPC or PCE

Select any commercially available pre-shredded pine cone material. Once the pre-shredded pine cone material is selected heat extraction of the defatted ground pine cone material is required. The heat extraction is performed in the presence of an aqueous solvent that contains potassium hydroxide. Once the pine cone material is extracted, particulate matter with an average particle size greater than 0.2 μm is removed. Then the pH of the resulting extract is adjusted to be between 6.0 and 8.0 to obtain the extract.

Shredded pine cone material is preferred because it facilitates subsequent extraction. Also, it is easily obtained because of its commercial availability. Further, shredded pine cone maintains sufficiently stable and uniform composition throughout several batches.

Prior to use in the purification procedure, the shredded pine cone material is washed. During the procedure the shredded pine cone material is washed twice with successive washings with about 10 liters of deionized water. The washed material is then defatted prior to extraction by washing once with 95% ethanol. Agitate the ethanol and washed pinecone material, then drain. Air-dry the cleaned pinecone material overnight. The defatted pine cone material is stored in a closed container at room temperature.

The defatted pine cones are preferably ground into small particles prior to the extraction step. This treatment facilitates release of active ingredients. Preferably the particle size should be in the range of 80–120 mesh.

The solvent for heat extraction of the pine cones is an aqueous solution comprising potassium hydroxide (KOH). The solution comprises at least 0.25% w/w potassium hydroxide, preferably it comprises 0.5–2% w/w potassium hydroxide, more preferably it comprises 1% w/w potassium hydroxide. The inventors have found that with these concentrations of potassium hydroxide, particularly effective extracts can be obtained. The pH of the solvent is preferably at least 8, more preferably at least 10, most preferably in the range of 11–13.

Extraction of the pine cone material is performed by adding solvent to the pine cones and heating the mixture, preferably to temperatures at or above 80° C. (176° F.). The inventors have found that extraction can be performed conveniently fast and with sufficient extraction rates when the solvent is boiling. It is particularly preferred to extract the pine material by autoclaving, that is at 121° C. This way a particularly fast, gentle and complete extraction of the active ingredients can be achieved.

After extraction it is convenient to allow the mixture to cool, preferably to room temperature. If necessary, the mixture can be stored in a refrigerator for 12 hours before further processing.

Particulate matter with average particle sizes greater than 0.20 μm is then removed from the mixture. This can be achieved by any particle separation method. The inventors have found that a particularly convenient and efficient way is a two step process, wherein in the first step coarse particulate matter is removed by filtration, the remaining unwanted particulate matter is then removed by centrifugation, preferably at 4° C.±2° C.

The resulting particle-depleted mixture is then treated to adjust the pH to between 6.0 and 8.0. This is preferably done by titration with 1 N HCL until the pH of the mixture is 7.0. During the neutralization process with HCL a by product of potassium chloride is generated and remains in the mixture. The mixture can then be distributed into packaging units.

The mixture can be sterilized after adjustment of pH. It is preferred to sterilize by autoclaving at 121° C., liquid cycle, for 20 minutes. Other sterilization techniques can also be applied, like irradiation, homogenization and the like.

The mixture can be stored after pH adjustment and optional sterilization. Long term storage stability is best ensured by storage at low temperatures, preferably at or below 4° C., even more preferably in a frozen state, most preferably at −20° C. It is, however, preferred not to store the mixture at all but to use it immediately.

Example of Pine Extract Production Method

Wash about 5 kg of the shredded pine cone material, available from International Forest company such as, lobolly pine, splash pine and longleaves pine, twice with successive washings with about 10 liters of deionized water and then once in 10 liters of 95% ethanol. Agitate the ethanol and washed pinecone material, then drain. Air-dry the cleaned pinecone material overnight. Grind up the clean pinecone material in a blender so as to obtain particle sizes between the range of 80 to 120 mesh. Take 600 grams of the clean, ground-up pinecone material and place in a flask. Add 4.5 liters of 1% KOH. Plug the opening of the flask with a cotton ball wrapped in cheese cloth. Autoclave the pinecone material in the 1% KOH for one hour with slow exhaust (liquid cycle, 121° C.). Allow the flask to cool. If the contents are not immediately processed further, the flask can be stored in a refrigerator at 4° C.

The large particles are filtered out of the autoclave suspension with a nylon mesh filter on a Buchner funnel attached to a suction flask with a vacuum applied thereto. Removal of the fine particles is preformed by centrifuging the filtrate, using a medium-speed centrifuge at 800 rpm for 10 min at 4° C. The resulting supernatant is poured off and processed further. The particulate matter is saved.

The resulting particle depleted mixture is then treated to is adjust the pH to between 6.0 and 8.0. This is preferably done by titration with the 1N HCL until the pH of the mixture is 7.0. The obtained substance is PPC or PCE which can be distributed into packaging units.

The mixture after adjustment of the pH and placed in a packaging unit at room temperature, may be sterilized by autoclaving in a pan of deionized water for 20 minutes (liquid cycle, 121° C.). Other sterilization techniques may be used, such as irradiation, homogenization and the like.

The mixture can be stored after pH adjustment and optional sterilization. Long term storage stability is best ensured by storage of the mixture at low temperature, preferably at or below 4° C., even more preferably in a frozen state, most preferably at −20° C. It is, however, preferred not to store the mixture at all but to use it immediately.

Analytical Procedure

The concentration of the lignin is obtained by reading absorbance in a spectrophotometer at 280 nm (blank with distilled water) and obtain a spectrum by scanning from 200–700 nm. The substance obtained is stored in a refrigerator.

HSV Infecton

The test system consists of Vero cells obtained form the American Type Culture Collection. HSV-1(F) was obtained from Dr. Bernard Roizman, University of Chicago. Virus stocks were prepared in Vero cells, and stock and tissue extracts were titered on Vero cell monolayers.

PPC or PCE (pine extract) is a brown colored liquid with an absorption shoulder at 260–280 nm. It dissolves in water, and mixtures of water and ethyl alcohol, and in acetone. It contains a complex of polysaccharides and polyphenylpropenoids. The molecular weight is determined by fast protein liquid chromatography (FPLC). The five main components molecular weights of: greater than 100, 21.0, 13.5, 3.6 and 2.1 kDa.

Anti-HSV Activity of PPC/PCE

Oral Administration of Extract.

The extract was administered in drinking water. Treatment was begun 5 days before infection and continued through the experiment, with water changed and fresh extract added daily. No toxicity of extract or reduction in the volumes of water drunk by the mice was observed at concentration of up to 250 ug/ml administered for up to 10 days.

Effect of PPC/PCE on HSV infection in animals 5 week old CBA/J mice were infected with HSV-1(F) on the cornea. The corneas were scarified 8–10 times with 30 g needle and 10 ul of virus inoculum, containing $10^4$-$10^6$ pfu, /eye of HSV-1(F) was dropped on each eye.

At extremely high inoculating doses of virus, $10^5$ and $10^6$ had little effect at concentrations of up to 250 ug/ml, as shown in FIG. 1. However, at lower inoculating doses of virus $10^4$, a significant reduction in virus titer was observed. The maxum effect was seen at the highest concentration of the extract tested, and was observed in one experiment following infection with $10^4$ pfu/eye; in this case, the geomeric mean titer of the eyes from treated mice was reduced 100 fold compared to untreated controls. In several repeated experiments, the reduction in titer was 3–5 fold. No differences were observed between results obtained from infection of male vs. female mice.

Dose Determination

Figure 2:
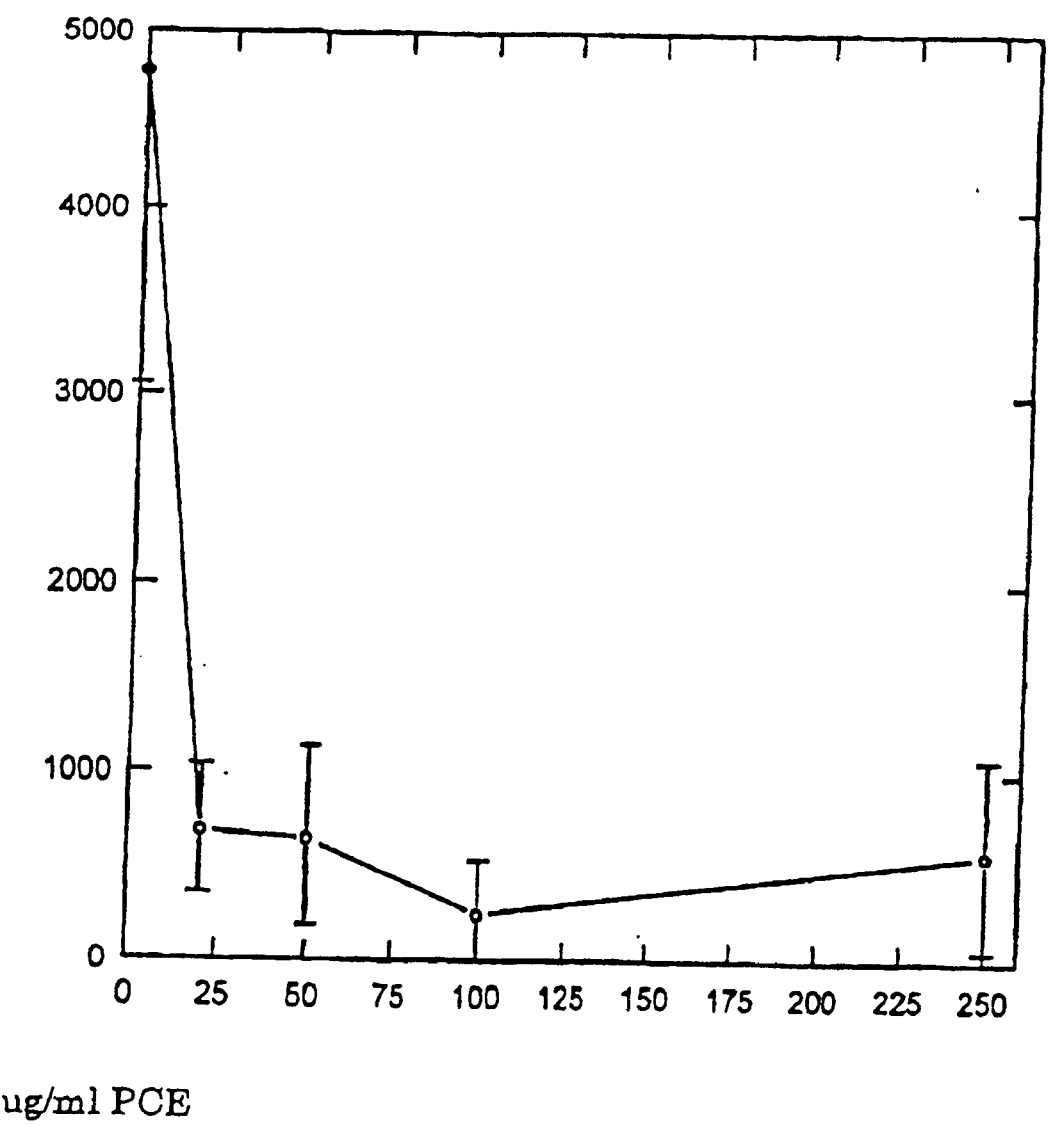
FIG. 2 shows the average titer of eyes 24 hours after infection following administration of varying concentrations of PCE extract.
Figure 3:
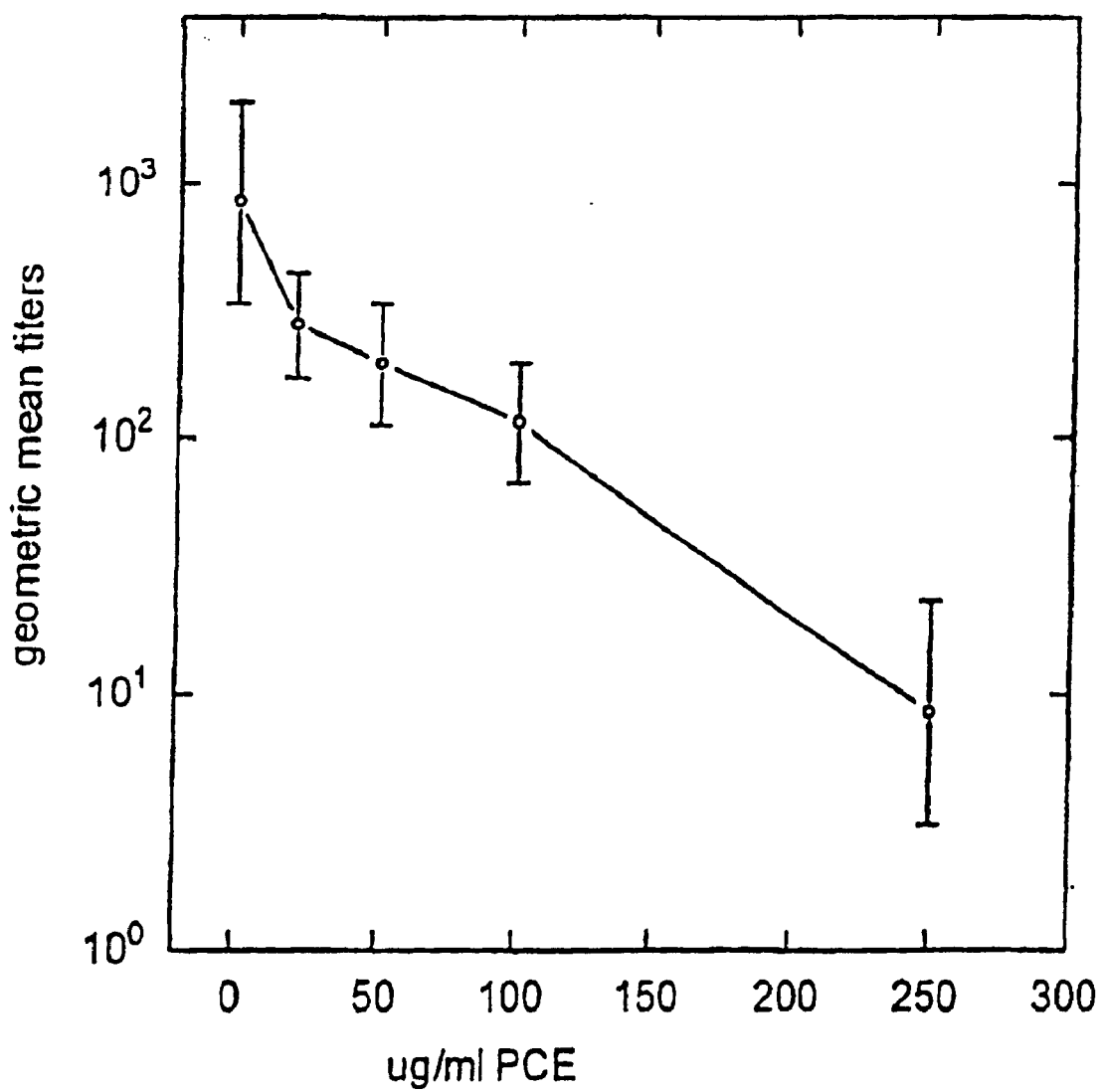
FIG. 3 shows the geometric mean titers of eyes 24 hours after infection following administration of varying amounts of extract.

To determine the optimum dose of the extract, mice were infected with $1 \times 10^4$ pfu/eye with administration of varying amounts of extract. No differences was observed in the efficacy of the extract administered at 20, 50, 100, 250 ug; titers of eyes in all treated groups were reduced approximately 8 fold as compared to controls (FIG. 2; p<0.05 for 250 ug/ml compared to controls). However, differences were observed in the geometric mean titers of virus obtained from the eyes, with a substantially lower titer obtained from mice treated with the highest dose of extract (250 ug/ml) as compared to those treated with the lowest dose (20 ug/ml, FIG. 3). This difference was due primarily to the presence in the 250 ug/ml group of several eyes from which no virus could be recovered, indicating that the extract had completely prevented infection of those eyes.

The present data demonstrate that under the conditions set out above, the PPC extract, prepared from potassium hydroxide extracts of pine cone, effectively reduced replication of HSV-1(F) in the mouse cornea. As described above, PPC of the present invention has potent anti-HSV activity. Therefore, it is highly probable that this agent would improve the condition of persons suffering from HSV and its effect might be augmented by combinational treatment with other chemotherapeutic agents (i.e. acyclovir, valaciclovir, penciclovir and famciclovir).

Therefore, the foregoing is considered as illustrative only of the principles of the invention. It is not intended to be exhaustive or to limit the invention to the precise forms disclosed. Obvious modifications or variations are possible in light of the above teachings. All such modifications and variations are within the scope of the invention as determined by the appended claims when interpreted in accordance with the breadth to which they are fairly, legally, equitably entitled.

We claim:

1. An anti-HSV agent comprising an extract from pine cones as the active component therein, whereby the extract is obtained by extraction of said pine cones with a solution of potassium hydroxide, and whereby said extract comprises potassium.

2. The anti-HSV agent as in claim 1, wherein said potassium hydroxide is a 1% solution of potassium hydroxide.

3. The anti-HSV agent as in claim 1, wherein said active component of said extract is polyphenylpropenoid-polysaccharide complex (PPC).

4. The anti-HSV agent as in claim 1, wherein said extract is extracted from pine cones of any variety or species of genus Pinus.

5. The anti-HSV agent as in claim 4, wherein the pine cone is selected from the group consisting of *P. densiflora, P. koraiensis, P. parviflora* and *P. thunbergii*.

6. The anti-HSV agent as set out in claim 3, wherein the polyphenylpropenoid-polysaccharide complex (PPC) has a brown color with an absorption shoulder at 260–280 nm, which dissolves in water and alcohol, and acetone, and is composed of a complex of polysaccharides and polyphenylpropenoids, with the five major components having a molecular weight of greater than about 100, 21.0, 13.5, 3.6 and 2.1 kilodaltons as determined by fast protein liquid chromatography, said polyphenylpropenoid-polysaccharide complex (PPC) being obtained from the precipitate from potassium hydroxide extract of pine cone at pH 7.

7. The anti-HSV agent of claim 1, wherein said extract has been extracted with potassium hydroxide having at least a pH of 8.

8. The anti-HSV agent of claim 7, wherein said potassium hydroxide has a pH of from 6 to 8.

9. A method of producing polyphenylpropenoid-polysaccharide complex (PPC) comprising the steps:

defatting a shredded pine cone material with an ethanol wash drying said pine cone material, after defatting, with air;

heat extracting a mixture of said pine cone with a 1% KOH solution after removal of ethanol and hot water extractable materials and air-drying for 24 hours;

removing particulate matter with an average particle size greater than 0.2 $\mu$m from said mixture; and adjusting the pH of the resulting particle-depleted mixture to between 6 and 8, potassium of said KOH remaining in said particle-depleted mixture.

10. An anti-I-ISV composition containing an effective amount of polyphenylpropenoid-polysaccharide complex (PPC) and potassium as obtained according to claim 9.

* * * * *